US010463309B2

United States Patent
Looney et al.

(10) Patent No.: US 10,463,309 B2
(45) Date of Patent: Nov. 5, 2019

(54) DUAL MODALITY SENSOR WITH BIOSENSING ELECTRODES

(71) Applicant: Imperial College Innovations Limited, London (GB)

(72) Inventors: David Looney, London (GB); Danilo Mandic, London (GB); Valentin Goverdovsky, London (GB)

(73) Assignee: Imperial College Innovations Limited, London (GB)

( * ) Notice: Subject to any disclaimer, the term of this patent is extended or adjusted under 35 U.S.C. 154(b) by 304 days.

(21) Appl. No.: 15/111,792

(22) PCT Filed: Jan. 14, 2015

(86) PCT No.: PCT/GB2015/050065
§ 371 (c)(1),
(2) Date: Jul. 14, 2016

(87) PCT Pub. No.: WO2015/107339
PCT Pub. Date: Jul. 23, 2015

(65) Prior Publication Data
US 2016/0331328 A1    Nov. 17, 2016

(30) Foreign Application Priority Data

Jan. 15, 2014 (GB) .................................. 1400646.4

(51) Int. Cl.
*A61B 5/00* (2006.01)
*A61B 5/0408* (2006.01)
*A61B 5/0478* (2006.01)
*A61B 5/0205* (2006.01)
*A61B 5/0492* (2006.01)
*A61B 5/1455* (2006.01)
*A61B 5/024* (2006.01)

(52) U.S. Cl.
CPC ............ *A61B 5/721* (2013.01); *A61B 5/0205* (2013.01); *A61B 5/0408* (2013.01);
(Continued)

(58) Field of Classification Search
CPC . A61B 5/0205; A61B 5/02416; A61B 5/0408; A61B 5/0478; A61B 5/0492;
(Continued)

(56) References Cited

U.S. PATENT DOCUMENTS

| 5,978,693 A | 11/1999 | Hamilton et al. |
| 2004/0032957 A1* | 2/2004 | Mansy ............... A61B 5/04085 381/67 |

(Continued)

FOREIGN PATENT DOCUMENTS

| EP | 2 783 725 A1 | 10/2014 |
| WO | 2004/052190 A1 | 6/2004 |
| WO | 2007/002116 A2 | 1/2007 |

OTHER PUBLICATIONS

Pengjun, X., et al., "Measurement of Wearable Electrode and Skin Mechanical Interaction Using Displacement and Pressure Sensors," 2011 4th International Conference on Biomedical Engineering and Informatics (BMEI), Shanghai, China, pp. 1131-1134, Oct. 2011.
(Continued)

*Primary Examiner* — Michael J Carey
(74) *Attorney, Agent, or Firm* — Perkins Coie LLP

(57) ABSTRACT

A dual modality sensor comprises a tissue-contact electrode having a first surface configured for receiving an electrical signal from a user's tissue when attached thereto; and a mechanical sensor overlying the cutaneous electrode and configured to sense a mechanical displacement of the first surface through the electrode. The electrode and the mechanical sensor thereby provide electrical and mechanical signals which originate from precisely the same tissue location.

19 Claims, 4 Drawing Sheets

(52) U.S. Cl.
CPC .......... *A61B 5/0478* (2013.01); *A61B 5/0492* (2013.01); *A61B 5/14552* (2013.01); *A61B 5/6843* (2013.01); *A61B 5/02416* (2013.01); *A61B 2562/0204* (2013.01); *A61B 2562/0209* (2013.01)

(58) Field of Classification Search
CPC ... A61B 5/14552; A61B 5/6843; A61B 5/721; A61B 2562/0204; A61B 2562/0209
USPC .................................................. 600/300, 301
See application file for complete search history.

(56) References Cited

U.S. PATENT DOCUMENTS

| | | | |
|---|---|---|---|
| 2006/0149146 A1* | 7/2006 | Schmidt | A61B 5/0006 600/372 |
| 2007/0049837 A1* | 3/2007 | Shertukde | A61B 5/0408 600/528 |
| 2008/0208028 A1 | 8/2008 | Thijs et al. | |
| 2011/0213273 A1* | 9/2011 | Telfort | A61B 7/003 600/586 |
| 2011/0270048 A1 | 11/2011 | Addison et al. | |

OTHER PUBLICATIONS

Daly, I., et al., "On the Automated Removal of Artifacts Related to Head Movement From the EEG," IEEE Transactions on Neural Systems and Rehabilitation Engineering, 21(3):427-434, May 2013.

UK Search Report dated Jul. 16, 2014 for UK Patent Application No. 1400646.4, filed on Jan. 15, 2014 (6 pages).

International Search Report and Written Opinion dated Apr. 21, 2015 for International Application No. PCT/GB2015/050065, filed on Jan. 14, 2015 (9 pages).

* cited by examiner

DUAL MODALITY SENSOR WITH BIOSENSING ELECTRODES

The present invention relates to electrodes for sensing electrical signals from human or animal tissue. Such electrodes are typically used as biomedical sensors for sensing electrical parameters from the human or animal body.

The global biomedical electrode market is substantial and the market for biosensors is several times bigger. Both dry and wet or gel-based electrodes tend to suffer from significant signal quality degradation from mechanical motion artefacts (noise) arising from, for example, relative motion between the electrode surface and the skin to which they are applied. Dry electrodes are more susceptible to this noise, which is disadvantageous since dry electrodes are often more convenient to use and are generally preferred for a number of applications. This is particularly the case where long-term electrode use is required, for extended durations of continuous monitoring, or where a user or non-specialist may be required to apply the electrodes, for example outside clinical and laboratory environments. Wet gel electrodes tend to be less suitable for extended monitoring as the gel dries out and the electrodes can no longer function.

Electrodes are widely used for applications such as electrocardiogram (ECG) recording, and the mechanical interaction, between electrode and skin is known to give rise to motion, artefacts which can significantly contaminate an ECG signal. In Pengjun Xu et al, "Measurement of wearable electrode and skin mechanical interaction using displacement and pressure sensors", 2011 4th International Conference on Biomedical Engineering and Informatics, an electrode assembly was described in which an ECG electrode, a pressure sensor and an optical displacement sensor were mounted together to create a wearable electrode assembly. The electrode has a hole at the centre to allow laser light to pass through from the optical displacement sensor and electrode-skin relative displacement is monitored thereby. The pressure sensor measured electrode-skin contact pressure. The effects of electrode-skin contact pressure and electrode-skin motion on ECG were studied.

It is an object of the invention to provide a biosensing electrode which enables reduction of motion artefact in an electrical signal output of the electrode.

According to one aspect, the present invention provides a dual modality sensor comprising:
 a tissue-contact electrode having a first surface configured for receiving an electrical signal from a user's tissue when attached thereto; and
 a mechanical sensor overlying the cutaneous electrode and configured to sense a mechanical displacement of the first surface through the electrode.

The electrode may comprise an electrically conductive layer defining a diaphragm of the mechanical sensor. The mechanical sensor may be configured to produce an electrical output as a function of displacement of the diaphragm out of the plane of the diaphragm at rest. The mechanical sensor may be configured to produce an electrical output as a function of a compression wave passing through the electrode. The diaphragm of the mechanical sensor may comprise a first wall of a chamber, the chamber having a second wall defined by a resilient membrane, the chamber providing acoustic coupling between the diaphragm and the resilient membrane. The mechanical sensor may comprise a vibration sensor, a microphone or a piezoelectric transducer. The diaphragm may further include an electrically insulating layer disposed between the electrically conductive layer and the mechanical sensor. The mechanical sensor may comprise a transducer and an electrically insulating layer disposed between the transducer and the tissue-contact electrode. The electrode may comprise a cutaneous electrode. The electrode may comprise conductive bio-compatible material. The mechanical sensor may be disposed on a carrier configured to retain, the electrode in contact with a user's tissue. The carrier may be configured to engage the first surface of the electrode to the user'skin.

According to another aspect, the invention provides a method of reducing noise in a bioelectrical signal from a tissue-contact electrode comprising:
 providing a dual modality sensor as defined above;
 disposing a first surface of the electrode against a user's tissue to receive a bioelectrical signal therefrom;
 receiving, from the mechanical sensor, a movement signal indicative of mechanical displacement of the electrode;
 using the movement signal to attenuate or remove motion artefact from the bioelectrical signal.

According to another aspect, the present invention provides a method of enhanced physiological sensing using a tissue-contact electrode comprising:
 providing a dual modality sensor as defined above;
 disposing a first surface of the electrode against a user's tissue to receive a bioelectrical signal therefrom;
 receiving, from the mechanical sensor, a movement signal indicative of mechanical displacement of the electrode;
 combining the bioelectrical signal and the movement signal to determine a physical property of the user.

Embodiments of the present invention will now be described by way of example and with reference to the accompanying drawings in which.

Figure 1:
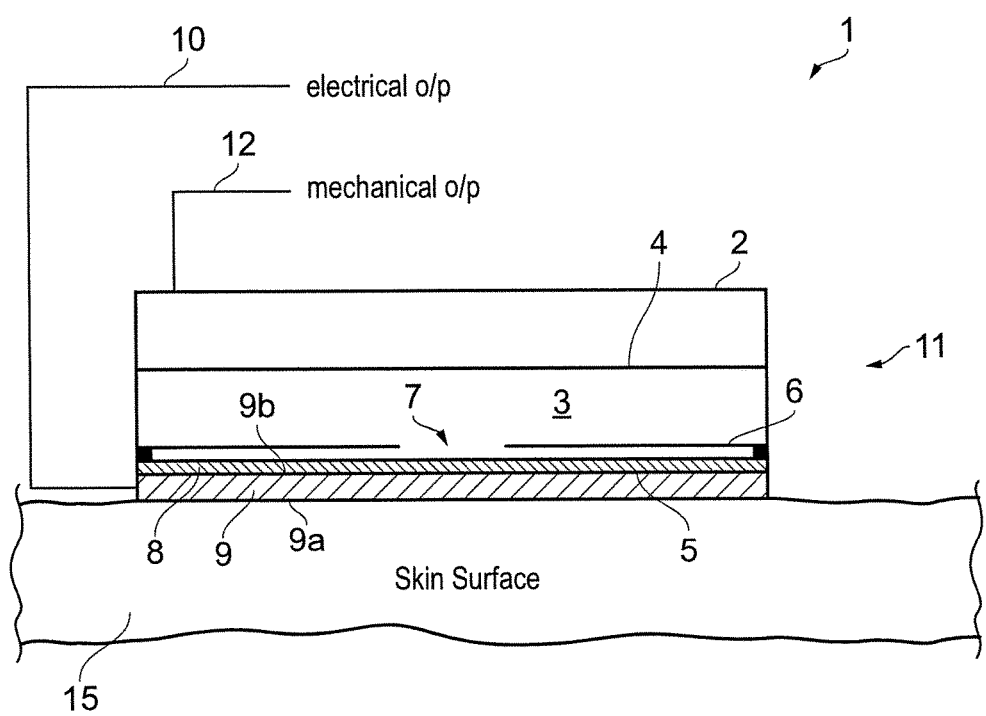
FIG. 1 shows a schematic cross-sectional view of a dual modality sensor with an electrode and an overlying mechanical sensor.

The illustrative embodiment of FIG. 1 shows a sensor that is configured to enable recording of electrical and mechanical activity simultaneously. This may be described as a dual modality, or multimodality, sensor. In particular, the electrical and mechanical activity are sensed from exactly the same location on a user's body, i.e. the sensors are co-located.

With reference to FIG. 1, a dual modality sensor 1 comprises a housing 2 defining an acoustic chamber 3 bounded at one end by a membrane 4 and at the other end by a diaphragm 5. The membrane 4 preferably has low or negligible inertia. The diaphragm 5 is disposed adjacent to, on, or forms part of, an internal wall 6 having an aperture 7 therein. The diaphragm 5 comprises an electrically conductive electrode 9 and an electrically insulating layer 6. The electrically conductive electrode 9 defines a first surface 9a which is exposed for contact with a user and a second surface 9b by which it is coupled to the electrically insulating layer. The insulating layer 8 could be omitted if the housing 2 and/or the internal wall 6 are electrically insulating.

The electrically conductive electrode 9 is configured to be usable as a biosensing electrode, preferably of low impedance. Throughout the present specification, the expression "biosensing electrode" is intended to encompass both biomedical electrodes, as well as other electrodes that can be attached to the human, or animal body but which are not necessarily used for strictly medical purposes, e.g. for use as human-machine interfaces. The electrode 9 provides an electrical output connection 10 which may be a direct wired connection, or may include integrated signal processing electronics, such as a pre-amplifier, an amplifier, an analogue to digital converter and/or a transmitter. The membrane 4, acoustic chamber 3 and diaphragm 5 together form part of a mechanical sensor 11 having an electrical output 12 from a transducer element, not shown, sensitive to vibration in the membrane 4. The electrical output 12 may be a direct connection to the transducer element output, or may include integrated signal processing electronics, such as a pre-amplifier, an amplifier, an analogue to digital converter and/or a transmitter.

The electrode 9 may comprise a layer of electrically conductive, flexible, polyurethane-based material coated on the diaphragm 5. Other conductive materials could be used.

In one arrangement, the mechanical sensor 11 comprises a condenser microphone. Other mechanical sensors could be used, such as other types of microphone, piezoelectric elements (transducers), accelerometers etc.

One arrangement uses the casing of the microphone as the housing 2 which serves as one of the electrical connections for connection to a power supply and is therefore coated with a spray-on insulator. Subsequently, the diaphragm 5 may be positioned on the microphone face with aperture 7, extending over the aperture, and copper wire bonded thereto to provide an electrical connection to the electrode 9. The electrode 9 provides a suitable contact surface which may be flat or curved, or more generally profiled to conform to the shape of the surface it is intended to be attached to.

As shown in FIG. 1, the sensor 1 is configured to be disposed against a user's skin surface 15, to operate as a cutaneous electrode. More generally, however, the sensor may be a tissue-contact electrode configured to be disposed against any suitable tissue structure on or in the human or animal body from which electrical signals may usefully be sensed, i.e. including both internal and external use.

Thus, in a general aspect, the sensor 1 is preferably provided with a carrier suitable for attachment of the sensor to the human or animal body to bring the electrode into contact with a suitable tissue structure, and to retain it in position. For a cutaneous electrode configuration, this may be an adhesive patch structure to provide adhesion, to the users skin. Alternatively, the carrier could be a wearable garment, belt, strap, bandage, cap or any other carrier suitable for attachment to the body. For an internal use sensor, the carrier may comprise a guidewire, probe, catheter or other suitable structure for introduction into the body.

The co-location of the electrical sensor (electrode 9) and the mechanical sensor 11 can be achieved by overlaying the two sensors, one on tope of the other as shown, so that the mechanical sensor senses displacement through the electrode. In one arrangement as shown in FIG. 1, the electrical and mechanical sensors are coaxial and coextensive, i.e. with co-located central axes and with the areal extent of both mechanical sensor and electrode substantially the same. In another arrangement, the mechanical sensor 11 could be somewhat smaller in area than the electrode 9, i.e. sensing mechanical displacement through only a portion of the electrode. In this case, the axes could be somewhat offset. In another arrangement, the mechanical sensor 11 could be somewhat larger in area than the electrode 9.

In use, the sensor 1 is positioned with the electrode surface 9a in contact with the requisite tissue structure. The electrode 9 may be a dry electrode or a wet gel electrode, and may be positioned in contact with the tissue with or without using a conductive paste, gel, wet or other layer to enhance electrically conductivity to the skin. The electrically conductive electrode receives electrical signals from the tissue structure with respect to a suitable reference, e.g. a second electrode which may be a reference electrode, a ground electrode or a second sensing electrode. The second electrode could be part of another dual modality sensor as described herein.

Any movement of the electrode surface 9a relative to the tissue, e.g. skin 15, or movement of the skin underlying the electrode, will result in displacements, typically small, of the electrode 9 out of the plane it occupies when at rest, herein referred to as out-of-plane displacement. Since the electrode forms part of the diaphragm 5, the out-of-plane displacements of electrode 9 necessarily result in corresponding out-of-plane displacements of the diaphragm 5. Such displacements are transmitted acoustically to the membrane 4. The membrane 4 preferably has sufficiently low or negligible inertia such that it is insensitive to movement of the user's whole body or limbs but is sensitive to the local movement of the electrode. The movement of membrane 4 is sensed by the transducer element (not shown) of which it may be a part, and electrical signals indicative of the mechanical displacement are generated on electrical output 12, referred to herein as movement signals indicative of mechanical displacement of the electrode.

Similarly, any acoustic wave, i.e. a longitudinal or compression wave, that is coupled from the tissue 15 into the electrode 9, is acoustically coupled to the mechanical sensor 11. In this respect, the compression wave can be considered to impart a mechanical displacement of the surface 9a of electrode 9 and the mechanical sensor senses this mechanical displacement of the surface 9a through the electrode.

Separate signal processing electronics and/or software, provided on electrical output 12, can be used to remove movement artefacts from the electrical signals sensed by the electrode 9 provided on electrical output 10.

The sensor is suitable for recording a wide range of electrical signals, such as electroencephalogram (EEG), electrocardiogram (ECG), electromyogram (EMS), etc. and a wide range of mechanical signals, such as venous pulsation, respiration, speech, etc and can also be used to derive additional biomedical parameters like pulse and blood pressure. Thus, the sensor can replace several individual sensors, reducing clutter and simplifying sensor attachment, and enabling key applications in emerging sensing systems. The dual modality sensor enhances the ability to record physiological electrical and mechanical activity for vulnerable populations for whom it is difficult to remain still during a recording session, such as new-borns, infants and the elderly.

An important feature of the dual modality sensor is the co-location of the sensing surfaces for both electrical and mechanical activity. Providing a measure of mechanical activity of the actual electrical sensing surface has been found to provide a substantial improvement in the ability to de-noise electrical signals sensed by the electrode, i.e. to remove or substantially attenuate motion artefact in the electrical signals.

The degradation of signal quality by motion artefacts is a well-known problem in biomedical sensing such as: (i)

EEG, the electrical recording of brain activity; and (ii) ECG, the electrical recording of cardiac activity. In particular, this is a major problem in EEG applications where the signal of interest is typically much weaker than artefacts caused by movement between the skin and electrode. With recordings in controlled laboratory environments, the subjects are routinely asked to remain as still as possible. Even eye movement or blinking can cause significant degradation of the EEG quality. Motion artefacts can also arise from muscle activity or whole-body or limb movement. The conventional way of dealing with motion-induced artefacts is to detect their onset and subsequently discard the contaminated part of the recording. Although effective, this approach reduces the size of datasets and introduces discontinuities in the data, resulting in potential loss of important information. In scenarios where the motion artefacts do not have large amplitudes, it can be difficult to distinguish the underlying EEG, which can lead to incorrect analysis. While the latest developments in electronics and the miniaturization of battery technology have brought commercially available wearable EEG devices, the electrode technology is still lagging, with motion artefacts remaining a significant obstacle.

A partial solution to head movement artefacts in EEG recordings already proposed detects movement with a tri-axial accelerometer. Ideally for EEG enhancement, only local electrode movements with respect to the skin should be used. This may not be the case for an accelerometer, which also picks up head and whole body movements as opposed to only the motion, of individual electrodes, compromising accuracy.

The sensor as described in this specification provides an electrode with an embedded mechanical sensor which picks up motion of the electrode relative to the user's body, e.g. out-of-plane displacements of the electrode along the skin-sensor interface. The output 12 of the mechanical sensor is completely electrically decoupled from the electrical output 10 of the electrode 9 and makes it possible to remove the displacement artefact from the electrical signal.

Preliminary results using the sensor configuration described herein indicate that motion artefacts can be removed from the electrical recording, via routine signal processing methods, to obtain a clean EEG signal and promise high quality continuous EEG recordings in natural environments, offering an improvement over accelerometer-based systems.

Figure 2:
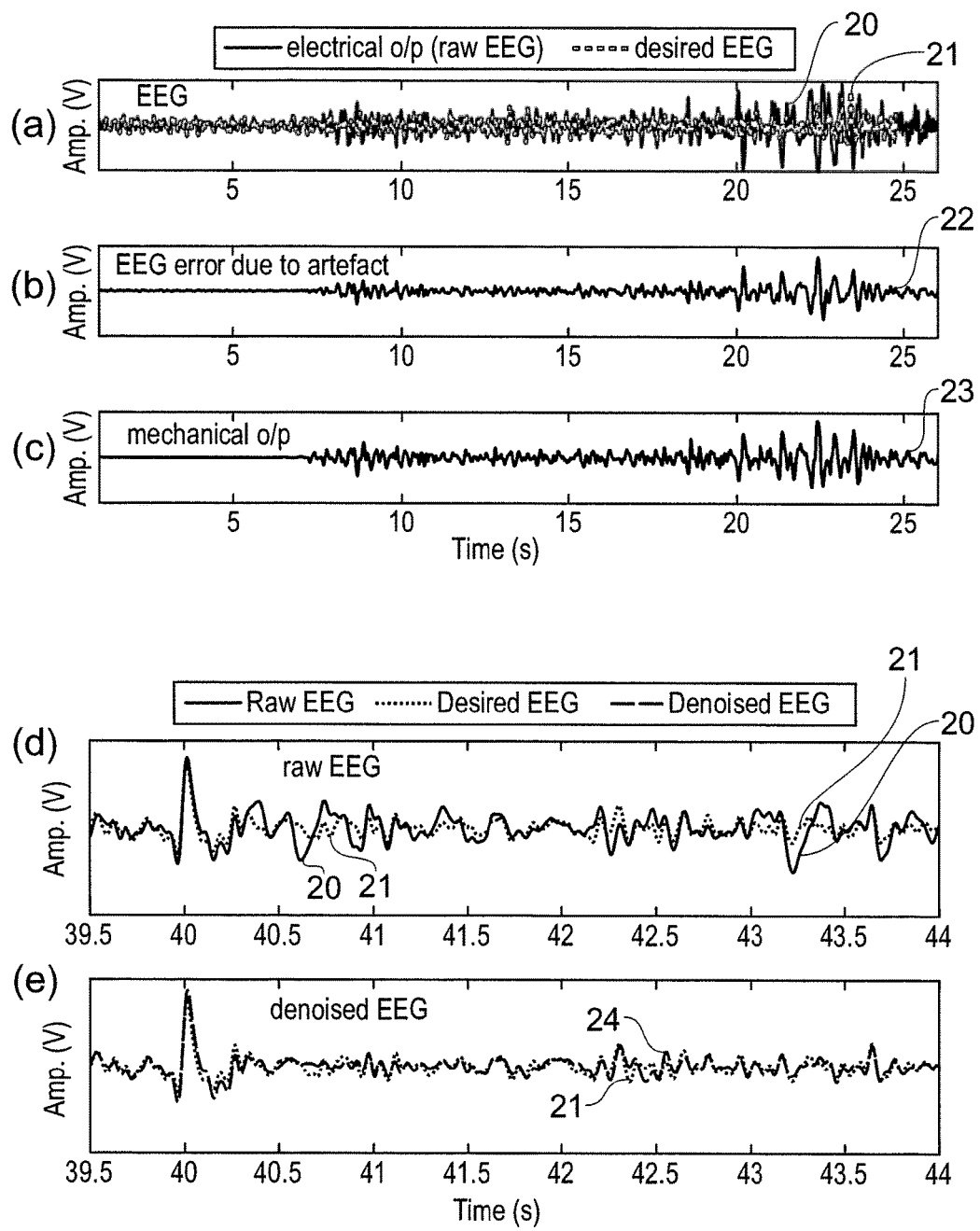
FIG. 2 shows graphically sensor outputs from the electrode and mechanical sensor of the dual modality sensor of FIG. 1, illustrating that the mechanical sensor output correlates well with motion artefact found in the electrode EEG signal, and can be used to de-noise the EEG signal.

FIG. 2 illustrates the performance of the dual modality sensor and demonstrates the possibility of de-noising an electrical signal from the electrode. FIG. 2a shows an EEG recording using the electrode 9, in which the trace 20 shows the electrical signal from the sensor 1, i.e. the raw EEG, which is subject to motion, artefacts. Trace 21 shows the corresponding waveform of the clean (desired) EEG signal without such motion artefacts. FIG. 2b shows trace 22 which is the error signal, i.e. the difference between the raw (noisy) EEG and the desired (clean) EEG. FIG. 2c shows trace 23 which is the output signal 12 from the mechanical sensor 11. There is a high degree of correlation between the mechanical sensor output signal 23 and the error signal 22. FIG. 2d shows an enlarged view of the noisy EEG (trace 20) and the desired EEG (trace 21). FIG. 2e shows an enhanced (de-noised) EEG signal 24 based on electrode output trace 20 but using the output 12 of the mechanical sensor 11 to remove motion artefact, compare with the desired (clean) EEG signal 21.

The EEG signal 20 was recorded with a sensor 1 placed on the user's forehead. The clean EEG signal 21 was obtained by placing four standard electrodes around the sensor 1 at equal distances of 3 cm from the sensor 1 and obtaining the averaged waveform.

By integrating multiple modalities into a single unit the sensor 1 is easier to use and less cumbersome or obtrusive. The mechanical sensor 11 has the body to which it is attached as a frame of reference which ensures high sensitivity to local mechanical activity, particularly to mechanical activity at the sensor-skin interface, while reducing sensitivity to whole body movements. The dual modality sensor 1 is suitable for integration with wearable sensing technology, and has small size, low weight and power. Through use of the multimodal sensor and use of signal processing, the electrode enables improvement in signal quality.

The dual modality sensor 1 may also be deployed for other uses. At present, local mechanical vein pulsations induced by cardiac activity are measured using pulse oximetry (PPG) sensors based on modulations in skin-absorbed light. Compared to ECG, which rewires two electrodes to be placed at distant positions on the body (at different sides of the heart), e.g. on the left and right arms, a single unit placed at one location is sufficient to monitor PPG. It has been found that the mechanical sensor 11 described above within the dual modality sensor 1 is able to record cardiac pulsations and may be considerably less sensitive to motion artefacts than PPG sensors. It can also be smaller and require less power.

Combining the recordings of electrical (ECG) and mechanical (PPG) attributes of cardiac function can provide new insights and enhanced physiological sensing, helping diagnose and monitor health-related conditions. Pulse arrival time (PAT)—the lag between ECG R-peak and PPG peak—is related to blood pressure as well as general health of the cardiovascular system. The distance between the adjacent PPG peaks can be used as a good proxy for heart rate variability, and has direct usage in the diagnosis of stress, fatigue and other aspects of autonomic cardiac function. Thus, the dual modality sensors described herein can be used to establish the above properties of cardiac function (PAT) in an enhanced physiological sensing technique.

Figure 3:
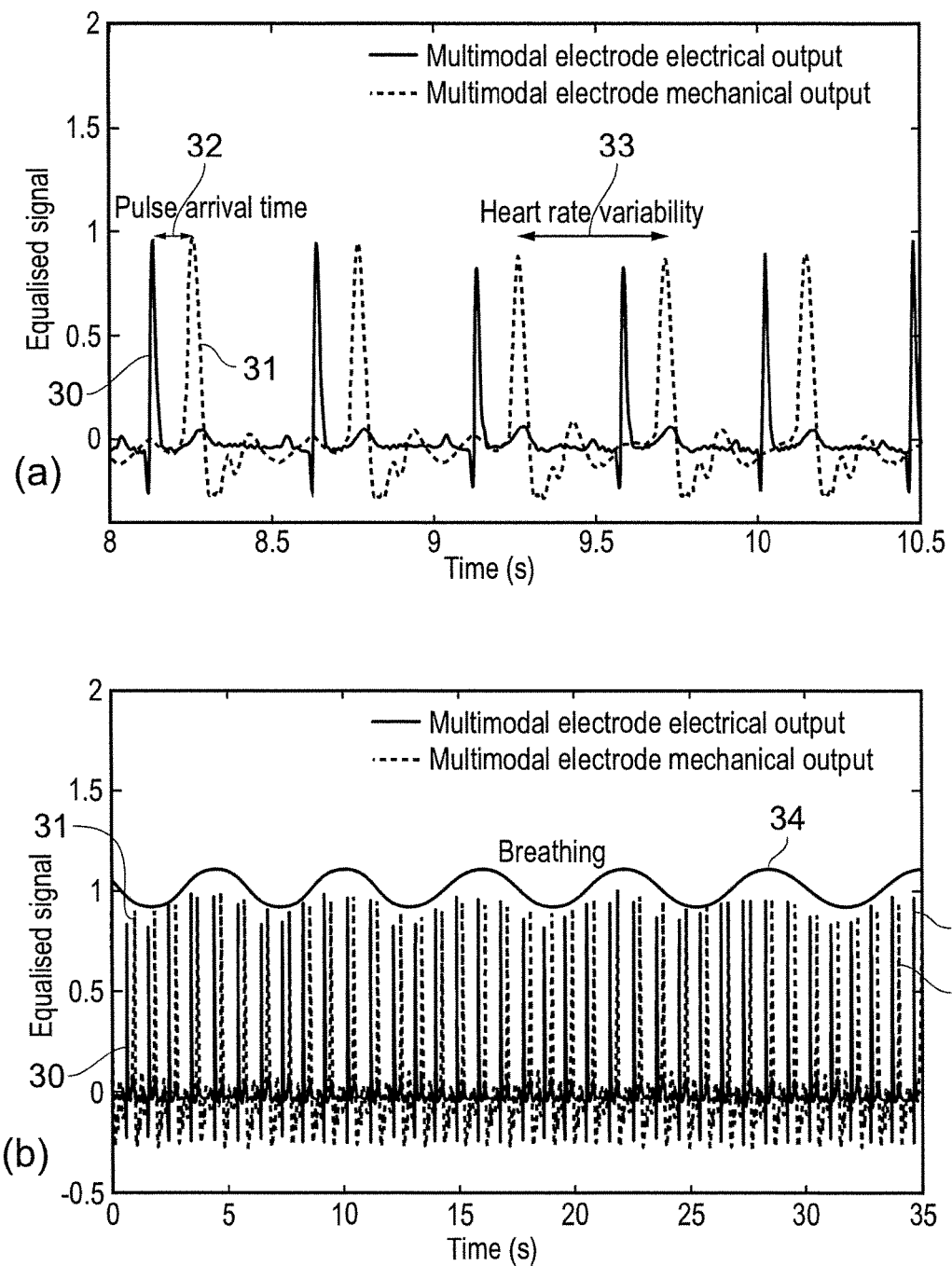
FIG. 3 shows graphically sensor outputs from the electrode and mechanical sensor of the dual modality sensor of FIG. 1, illustrating that pulse arrival time, heart rate variability and breathing rate can be obtained.

FIG. 3 illustrates results for multi-modal diagnosis using the sensor 1. FIG. 3a shows the electrode 9 electrical output 10 as ECG trace 30 and the mechanical sensor 11 output 12 as trace 31 indicating venous pulsation. Pulse arrival time (PAT) 32 can be derived using both modalities by calculating a time difference between respective pulses in the electrode signal 30 and the mechanical sensor signal 31, and is indicative of the blood pressure and general health of the cardiovascular system. Heart rate variability 33 can be calculated from either or both the electrode signal 30 and the mechanical sensor signal 31. Improved accuracy may be available using both signals 30, 31 which enhances physiological sensing. FIG. 3b illustrates that heart rate variability (HRV), pulse rate and breathing can be derived from the sensor's electrode signal 30, from the mechanical sensor signal 31, or from both providing greater accuracy and thus enhanced physiological sensing. The breathing signal 34 is obtained from modulation in the signals 30 and/or 31. For the physiological parameters HRV, pulse rate and breathing, the sensor uses a single location on the subjects body as opposed to at least two for ECG, thereby enabling easier data collection and potentially greater accuracy.

Thus, in a general aspect, such as particularly exemplified by FIG. 2, it can be seen that combining the electrode sensed data and the mechanical sensor data facilitates a method of reducing noise in a bioelectrical signal (such as EEG, or heart rate) from a single, or several, tissue-contact electrodes disposed against a user's tissue by combining the bioelectrical signal and the movement signal, e.g. by weighted averaging, to determine a physical property of the user such as brain function, heart rate, or heart rate variability.

In another general aspect, such as particularly exemplified by FIG. 3, it can be seen that the dual modality sensor facilitates a method of enhanced physiological sensing from a single tissue-contact electrode disposed against a user's tissue by combining the bioelectrical signal and the movement signal to determine with enhanced accuracy a physical property of the user such as heart rate, heart rate variability, respiration or blood pressure.

The sensor described herein can be manufactured to be no bigger or heavier than a standard biomedical electrode. It can be manufactured to be unobtrusive, cheap and disposable.

Although the sensors described herein have an acoustic chamber 3 coupling the electrode 9/diaphragm 5 to a transducer membrane 4, the sensor could be manufactured with the electrode 9 disposed directly onto a transducer surface of the mechanical sensing component, without an acoustic chamber, dependent on sensitivity requirements and structural compatibility.

In general, any mechanical sensor can be used which is capable of sensing an out-of-plane vibration or oscillation in the electrode (i.e. displacement out of the plane of the electrode at rest) or an acoustic compression wave passing through the electrode which creates localised out-of-plane vibration or oscillation in the electrode surface.

Figure 4:
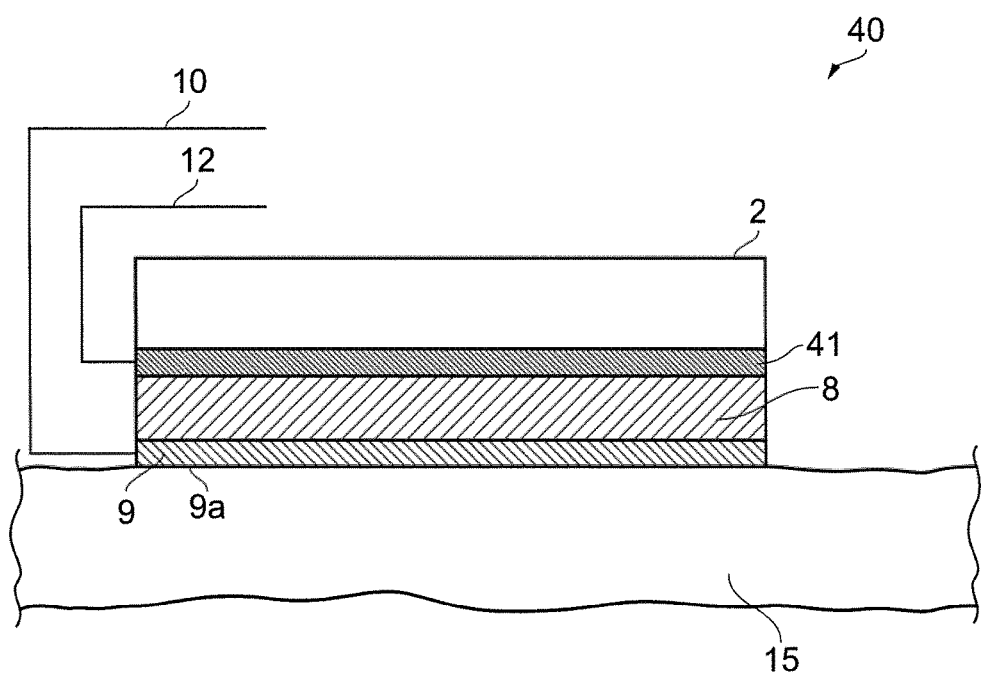
FIG. 4 shows a schematic cross-sectional view of a dual modality sensor with an electrode and an overlying mechanical sensor.

A further example is shown in FIG. 4. FIG. 4 shows a dual modality sensor 40 having an electrically conductive electrode 9, an electrically insulating layer 8, and a mechanical transducer element 41, which converts mechanical energy to electrical energy. The electrically conductive electrode defines a first surface 9a which is exposed for contact with a user, e.g. the user's skin 16 as shown in FIG. 4. The transducer element 41 provides the electrical output 12 of a mechanical sensor 11. The mechanical sensor 11 may be said to comprise the transducer 41 and any coupling entity (e.g. insulating layer 8) to the electrode 9 so that the mechanical sensor can sense any mechanical displacement of the electrode surface 9a through the electrode 9.

In the arrangement of FIG. 4, it can be seen that the coupling entity (insulating layer 8) effectively substitutes for the acoustic chamber 3 of the arrangement of FIG. 1, and ensures that any mechanical displacement of the electrode 9 (e.g. compression wave therein) is conveyed to the transducer element 41.

In the embodiments described, the electrode is preferably a low impedance electrode. The electrode material can be any conductive, bio-compatible material. An example could be a silver chloride electrode. Another example could be an electrode formed using a sintered powder material. The sintered powder material could be disposed onto a substrate such as copper.

Although the sensors described have dual modality, in providing both electrical sensing and mechanical sensing, the sensors can be adapted to include more than two modalities by inclusion of further types of sensor or transducer, integrated into the same housing or onto the same carrier, capable of sensing of further different physical parameters, e.g. accelerometers, temperature, pressure, optical sensors etc.

In a general aspect, obtaining an output from the dual modality sensor described herein may require the use of a second sensor as an appropriate reference. An output reflecting electrical activity at the sensor-tissue interface can be obtained by determining relative sensing differences between the electrode surfaces of two such dual modality sensors, or one such dual modality sensor and a standard electrode. Multiple such dual modality sensors (or multi-modality sensors) as described herein can be used simultaneously for collocated sensing at multiple points in or on the body. The dual modality sensors (or multi-modality sensors) as described herein can also be used as single modality sensors i.e. using only one of the outputs, for any particular application, e.g. where only a single modality is required at a particular point. For example, this could be in an array of single modality, dual modality or multi-modality sensors distributed across a user's body.

Applications can include making robust electrical recordings for a diverse range of clinical applications such as monitoring epilepsy events, characterising sleep disorders etc, and for a diverse range of clinical or non-clinical applications such as brain-computer interfaces, e.g. enabling communication pathways for the physically disabled and next-generation gaming.

Other embodiments are intentionally within the scope of the accompanying claims.

The invention claimed is:

1. A dual modality sensor comprising:
a tissue-contact electrode having a first surface configured for receiving an electrical signal from a user's tissue when attached thereto; and
a mechanical sensor overlying the tissue-contact electrode and configured to sense a mechanical displacement of the first surface through the electrode, the mechanical sensor comprising an acoustic chamber being bounded by a diaphragm on which the tissue-contact electrode is formed,
wherein the diaphragm comprises a first wall of the acoustic chamber, the chamber having a second wall defined by a resilient membrane, the chamber providing acoustic coupling between the diaphragm and the resilient membrane such that the mechanical displacement of the first surface through the electrode is transmitted acoustically via the diaphragm to the resilient membrane for sensing by a transducer element, and
wherein the tissue-contact electrode and the mechanical sensor are electrically decoupled.

2. The sensor of claim 1 in which the electrode comprises an electrically conductive layer defining the diaphragm of the mechanical sensor.

3. The sensor of claim 2 in which the mechanical sensor is configured to produce an electrical output as a function of displacement of the diaphragm out of the plane of the diaphragm at rest.

4. The sensor of claim 1 in which the mechanical sensor is configured to produce an electrical output as a function of a compression wave passing through the electrode.

5. The sensor of claim 1 in which the mechanical sensor comprises a condenser microphone.

6. The sensor of claim 2 in which the diaphragm further includes an electrically insulating layer disposed between the electrically conductive layer and the mechanical sensor.

7. The sensor of claim 1 in which the mechanical sensor comprises a transducer and an electrically insulating layer disposed between the transducer and the tissue-contact electrode.

8. The sensor of claim 1 in which the electrode comprises a cutaneous electrode.

9. The sensor of claim 1 in which the electrode comprises conductive bio-compatible material.

10. The sensor of claim 1 in which the mechanical sensor is disposed on a carrier configured to retain the electrode in contact with a user's tissue.

11. The sensor of claim 10 in which the carrier is configured to engage the first surface of the electrode to the user's skin.

12. A method of reducing noise in a bioelectrical signal from a tissue-contact electrode comprising:
providing a dual modality sensor comprising a tissue-contact electrode having a first surface configured for receiving an electrical signal from a user's tissue when attached thereto, and a mechanical sensor overlying the tissue-contact electrode and configured to sense a mechanical displacement of the first surface through the electrode, the mechanical sensor comprising an acoustic chamber being bounded by a diaphragm on which the tissue-contact electrode is formed, wherein the diaphragm comprises a first wall of the acoustic chamber, the chamber having a second wall defined by a resilient membrane, the chamber providing acoustic coupling between the diaphragm and the resilient membrane such that the mechanical displacement of the first surface through the electrode is transmitted acoustically via the diaphragm to the resilient membrane for sensing by a transducer element, and wherein the tissue-contact electrode and the mechanical sensor are electrically decoupled;
disposing a first surface of the electrode against the user's tissue to receive a bioelectrical signal therefrom;
receiving, from the mechanical sensor, a movement signal indicative of mechanical displacement of the electrode; and
using the movement signal to attenuate or remove motion artefact from the bioelectrical signal.

13. A method of enhanced physiological sensing using a tissue-contact electrode comprising:
providing a dual modality sensor comprising a tissue-contact electrode having a first surface configured for receiving an electrical signal from a user's tissue when attached thereto, and a mechanical sensor overlying the tissue-contact electrode and configured to sense a mechanical displacement of the first surface through the electrode, the mechanical sensor comprising an acoustic chamber being bounded by a diaphragm on which the tissue-contact electrode is formed, wherein the diaphragm comprises a first wall of the acoustic chamber, the chamber having a second wall defined by a resilient membrane, the chamber providing acoustic coupling between the diaphragm and the resilient membrane such that the mechanical displacement of the first surface through the electrode is transmitted acoustically via the diaphragm to the resilient membrane for sensing by a transducer element, and wherein the tissue-contact electrode and the mechanical sensor are electrically decoupled;
disposing a first surface of the electrode against the user's tissue to receive a bioelectrical signal therefrom;
receiving, from the mechanical sensor, a movement signal indicative of mechanical displacement of the electrode; and
combining the bioelectrical signal and the movement signal to determine a physical property of the user.

14. The method of claim 12, wherein the electrode comprises one of an electrically conductive layer defining the diaphragm of the mechanical sensor or a cutaneous electrode, or a conductive bio-compatible material.

15. The method of claim 12, wherein the mechanical sensor is configured to produce an electrical output as a function of a compression wave passing through the electrode.

16. The method of claim 12, wherein the mechanical sensor comprises a condenser microphone, or a transducer such that an electrically insulating layer disposed between the transducer and the tissue-contact electrode is disposed on a carrier configured to retain the electrode in contact with the user's tissue.

17. The method of claim 13, wherein the electrode comprises one of an electrically conductive layer defining a diaphragm of the mechanical sensor or a cutaneous electrode, or a conductive bio-compatible material.

18. The method of claim 13, wherein the mechanical sensor is configured to produce an electrical output as a function of a compression wave passing through the electrode.

19. The method of claim 13, wherein the mechanical sensor comprises a condenser microphone, or a transducer such that an electrically insulating layer disposed between the transducer and the tissue-contact electrode is disposed on a carrier configured to retain the electrode in contact with the user's tissue.

* * * * *